(12) United States Patent
Weber

(10) Patent No.: US 9,005,546 B2
(45) Date of Patent: Apr. 14, 2015

(54) FLOW CELL HAVING INTEGRATED FLUID RESERVOIR

(75) Inventor: Lutz Weber, Zweibrücken (DE)

(73) Assignee: Thinxxs Microtechnology AG, Zweibrücken (DE)

( * ) Notice: Subject to any disclaimer, the term of this patent is extended or adjusted under 35 U.S.C. 154(b) by 561 days.

(21) Appl. No.: 13/202,298

(22) PCT Filed: Dec. 16, 2009

(86) PCT No.: PCT/DE2009/001796
§ 371 (c)(1),
(2), (4) Date: Aug. 18, 2011

(87) PCT Pub. No.: WO2010/094249
PCT Pub. Date: Aug. 26, 2010

(65) Prior Publication Data
US 2011/0303306 A1    Dec. 15, 2011

(30) Foreign Application Priority Data

Feb. 19, 2009    (DE) .......................... 10 2009 009 728

(51) Int. Cl.
| | |
|---|---|
| *B01L 3/00* | (2006.01) |
| *B65D 35/00* | (2006.01) |
| *B65D 37/00* | (2006.01) |
| *G01N 21/05* | (2006.01) |
| *G01N 21/03* | (2006.01) |

(52) U.S. Cl.
CPC .......... *G01N 21/05* (2013.01); *B01L 3/502707* (2013.01); *B01L 3/50273* (2013.01); *B01L 2200/027* (2013.01); *B01L 2200/12* (2013.01); *B01L 2200/16* (2013.01); *B01L 2300/0877* (2013.01); *B01L 2300/088* (2013.01); *B01L 2400/0481* (2013.01); *G01N 2021/056* (2013.01); *G01N 2021/058* (2013.01); *G01N 2021/0346* (2013.01)

(58) Field of Classification Search
USPC .............. 222/94, 95, 93, 92, 207, 214, 514.6, 222/541.7, 107; 383/119; 137/343; 422/502, 503, 504, 505
See application file for complete search history.

(56) References Cited

U.S. PATENT DOCUMENTS

| | | | | |
|---|---|---|---|---|
| 4,328,912 | A * | 5/1982 | Haggar et al. ................ | 222/212 |
| 4,378,069 | A * | 3/1983 | Franco .......................... | 383/207 |

(Continued)

FOREIGN PATENT DOCUMENTS

| | | |
|---|---|---|
| DE | 202004000591 U1 | 3/2004 |
| DE | 10336849 A1 | 3/2005 |

(Continued)

*Primary Examiner* — Kevin P Shaver
*Assistant Examiner* — Stephane E Williams
(74) *Attorney, Agent, or Firm* — Lucas & Mercanti, LLP; Klaus P. Stoffel

(57) ABSTRACT

A flow cell having a support surface, and an integrated fluid reservoir made of two foil layers arranged on the support surface and joined with each other to enclose a storage space and a transport channel. The transport channel extends from a burst point that closes the storage space to a connecting opening and can be opened by fluid flowing from the storage space. A first of the foil layers of the fluid reservoir faces away from the support surface and projects beyond a second of the foil layers of the fluid reservoir that faces the support surface, and is bonded with the support surface in a projecting region.

15 Claims, 5 Drawing Sheets

(56) References Cited

U.S. PATENT DOCUMENTS

| | | | |
|---|---|---|---|
| 4,491,245 A * | 1/1985 | Jamison | 222/107 |
| 4,988,016 A * | 1/1991 | Hawkins et al. | 222/92 |
| 6,663,019 B2 * | 12/2003 | Garcia et al. | 239/327 |
| 6,667,081 B1 * | 12/2003 | Aoki et al. | 428/34.1 |
| 7,325,703 B2 * | 2/2008 | Gherdan et al. | 222/94 |
| 7,595,871 B2 | 9/2009 | Weber | |
| 2007/0224084 A1 | 9/2007 | Holmes et al. | |

FOREIGN PATENT DOCUMENTS

| | | |
|---|---|---|
| DE | 10336850 A1 | 3/2005 |
| DE | 102007059533 A1 * | 12/2007 |
| DE | 102009005874 A1 | 7/2010 |
| EP | 0583833 A2 | 2/1994 |
| WO | 02068823 A1 | 9/2002 |

* cited by examiner

2

FLOW CELL HAVING INTEGRATED FLUID RESERVOIR

The present application is a 371 of International application PCT/DE2009/001796 filed Dec. 16, 2009, which claims priority of DE 10 2009 009 728.7, filed Feb. 19, 2009, the priority of these applications is hereby claimed and these applications are incorporated herein by reference.

BACKGROUND OF THE INVENTION

The invention concerns a flow cell with integrated fluid reservoir that comprises two foil layers arranged on a support surface and joined with each other to enclose a storage space and a transport channel, wherein the transport channel extends from a burst point that closes the storage space to a connecting opening and can be opened by fluid flowing from the storage space.

A flow cell of this type is disclosed by German Patent Application DE 10 2009 005 874.5 of the present applicant, which is herewith incorporated by reference. The fluid reservoir, which consists of two foil layers, is adhesively bonded with the support surface by means of the foil layer that faces the support surface. In the area of the transport channel, the foil layers lie against each other unbonded. After the rupture of the burst point, fluid flowing from the storage space expands the transport channel, and a flow cross section forms. This allows the fluid reservoir to empty in a metered way and, above ail, bubble-free.

SUMMARY OF THE INVENTION

The objective of the invention is to create a new flow cell of the aforementioned type, the production of which is less complicated.

This objective is achieved with the flow cell of the invention, which is characterized in that the foil layer of the fluid reservoir that faces away from the support surface projects beyond the foil layer of the fluid reservoir that faces the support surface and is bonded with the support surface in this projecting region.

In accordance with the invention, a projecting region of the foil layer that faces away from the support surface is thus formed and used to join the fluid reservoir with the support surface. In this regard, it is advantageous if a joining means that serves to join the foil layers with each other is also used to join the fluid reservoir with the support surface.

The fluid reservoir is preferably joined with the support surface exclusively in the projecting region of the foil layer that faces away from the support surface, and preferably a welded joint is present between the fluid reservoir and the support surface as well as between the foil layers.

It is advantageous for this welded joint to be produced by means of a fusible coating on the foil layer or layers of the type usually present on aluminum foil used for the production of blister packs, i.e., for example, a layer of heat seal lacquer or hot melt adhesive on the foils, by which the layers of foil can be welded together, can also be used to weld the fluid reservoir with the support surface by virtue of the fact that this fusible coating faces the foil layer that faces away from the support surface in the projecting region of the support surface.

The support surface can be formed by a flat surface of a preferably plate-shaped flow cell, and the flat surface may be provided with a recess for receiving the foil layer that faces the support surface, so that this foil layer is flush with the flat surface.

In one embodiment of the invention, the foil layer that faces away from the support surface is suitably shaped to form a storage space and preferably comprises a projection in the form of a spherical cap.

Alternatively, the foil layer that faces the support surface can be shaped to form the storage space, and the aforementioned plate-shaped flow cell is provided with a depression that takes this shaping into account. For example, a projecting spherical cap that forms the storage space then passes through the depression formed as a passage through the plate, and the fluid reservoir is accessible for emptying by squeezing out the fluid.

The aforementioned connecting opening can be in direct or indirect fluid connection with a passage perpendicular to the support surface and/or with a channel of the flow cell that is parallel to the support surface.

In one embodiment of the invention, the channel, which is formed as a groove in the surface of the plate, is covered fluidtight by the projecting region of the foil layer that faces away from the support surface.

In the production of the flow cell described above, it is advantageous to prefabricate the fluid reservoir and to join it as a whole with the support surface of the flow cell. In the prefabrication of the fluid reservoir with the joining together of the foil layers, the foil layer that faces the support surface can be punched out to its final size by limited punch stroke after it has been joined with the other foil layer or immediately joined in its final dimensions with the other foil layer.

The flow cell described above allows fluids to be supplied, processed and analyzed in amounts of a few microliters to a few milliliters, with potential medical, diagnostic, analytical and cosmetic applications as well as use in miniaturized fuel cells and in the area of food packaging.

The invention is described in greater detail below with reference to the specific embodiments illustrated in the accompanying drawings.

DETAILED DESCRIPTION OF THE INVENTION

Figure 1:
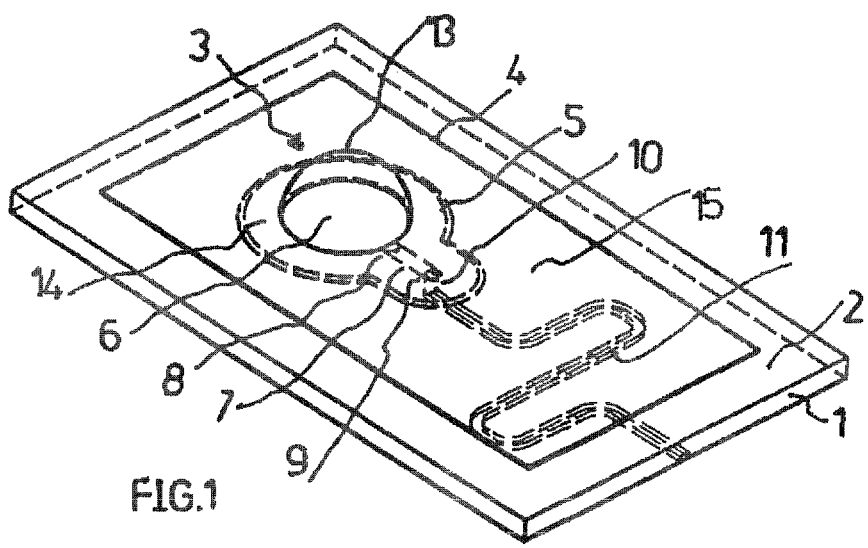
FIG. 1 is a first embodiment of a flow cell with an integrated fluid reservoir in accordance with the invention.

The flow cell shown in FIG. 1 comprises a plastic plate-shaped body 1 with a flat surface, which serves as a support surface 2 for a fluid reservoir 3 integrated in the flow cell.

The fluid reservoir 3 consists of two joined foil layers 4 and 5, between which a storage space 6 and a transport channel 7 are formed. The transport channel 7 extends from a burst point 8 that closes the storage space 6 to a connecting opening 9. The storage space 6 is formed by forming a projecting spherical cap 13 in the foil layer 4.

The connecting opening 9 is in fluid connection with a passage 10 that is perpendicular to the plane of the plate. A cover foil 12 on the side of the plate that faces away from the fluid reservoir 3 seals the channel 11, which is formed by a groove in the plate-shaped body 1, so that it is fluidtight towards the outside.

In the illustrated embodiment, the foil layers 4, 5 consist of aluminum foil with a fusible coating on one side, as used in the production of blister packs. The coating consists, for example, of a heat seal lacquer, a hot melt adhesive, or a fusible plastic, such as PE or PP.

Figure 2:
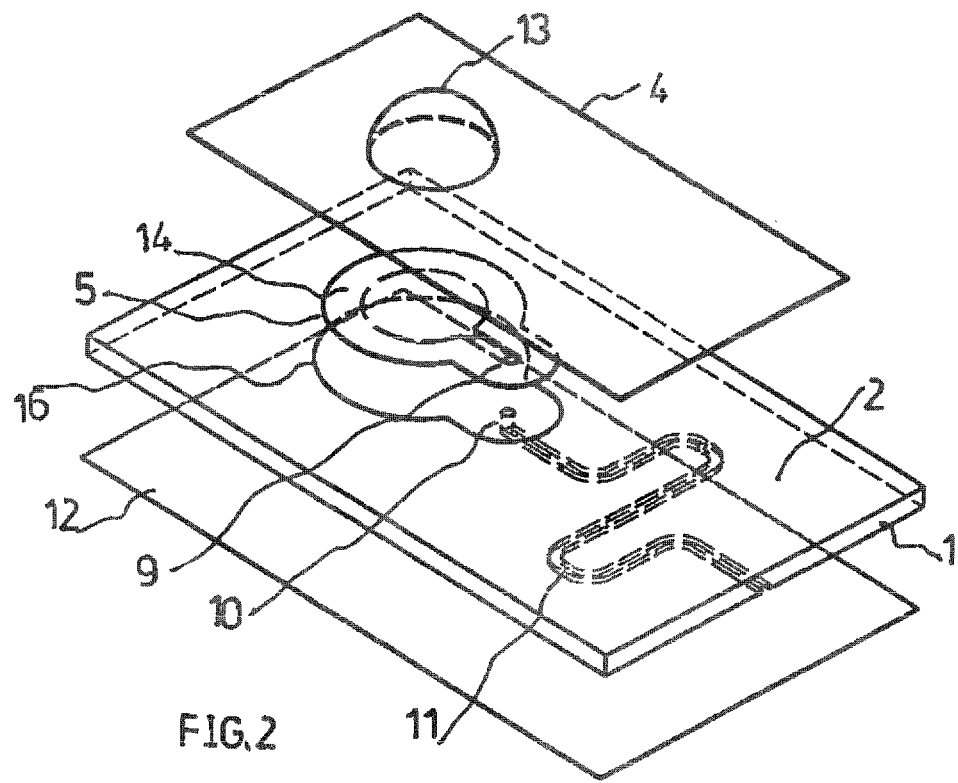
FIG. 2 is an exploded view of the flow cell of FIG. 1.

As FIGS. 1 and 2 show, the foil layer 4 that faces away from the support surface 2 has a projection 13 in the form of a spherical cap, which forms the storage space 6, while the foil layer 5 that faces the support surface 2 rests within a recess 16 with its entire area against the flat support surface 2. FIGS. 1 and 2 further show that the foil layer 4 that faces away from the support surface 2 extends laterally beyond the foil layer 5 in a region 15.

The foil layers 4, 5 are welded fluidtight by means of the aforementioned fusible coating in a closed region 14 that surrounds the storage space 6 and the transport channel 7. In the region 15 of the foil layer 4 that projects beyond the foil layer 5, a fluidtight welded joint between the foil layer 4 and the support surface 2 is produced by the same coating. The dimensions of the recess 16 are approximately the same as those of the foil layer 5, with the lateral dimensions of the recess 16 extending slightly beyond the lateral dimensions of the foil layer 5.

To produce the flow cell of FIG. 1, the fluid reservoir 3, which comprises the foil layers 4, 5, can be completely prefabricated, and the foil layer 5 can be welded with the foil layer 4, which has previously been shaped to form the storage space 6. As part of this prefabrication, the burst point 8 can be precisely produced in such a way that the storage space 6 is opened to the transport channel 7 at a predetermined internal pressure.

The foil layer 5 can already have the final dimensions shown in FIGS. 1 and 2 at the time it is being welded with the foil layer 4. However, handling can be simplified by using a foil 5 that is initially congruent to the foil layer 4. After this congruent foil 5 has been welded with the foil layer 4, the outer regions of the foil 5 that are not welded with the foil layer 4 are punched out by a suitable limited punch stroke, i.e., by the kiss cut method.

When pressure is applied by pressing the foil layer 4 in the area of the storage space 6, the burst point 8 is opened, and fluid flows into the channel 7, in the vicinity of which the foil layers 4 and 5 are not welded together. The foil layers, which rest against each other, are widened by the fluid flowing in, and a flow cross section opens by itself. The fluid passes through the connecting opening 9 and enters the passage 10 and thus the processing areas of the flow cell.

The illustrated flow cell serves only as an example and, in particular, can have additional cavities reached via the illustrated passage 10 and channel 11.

Figure 3:
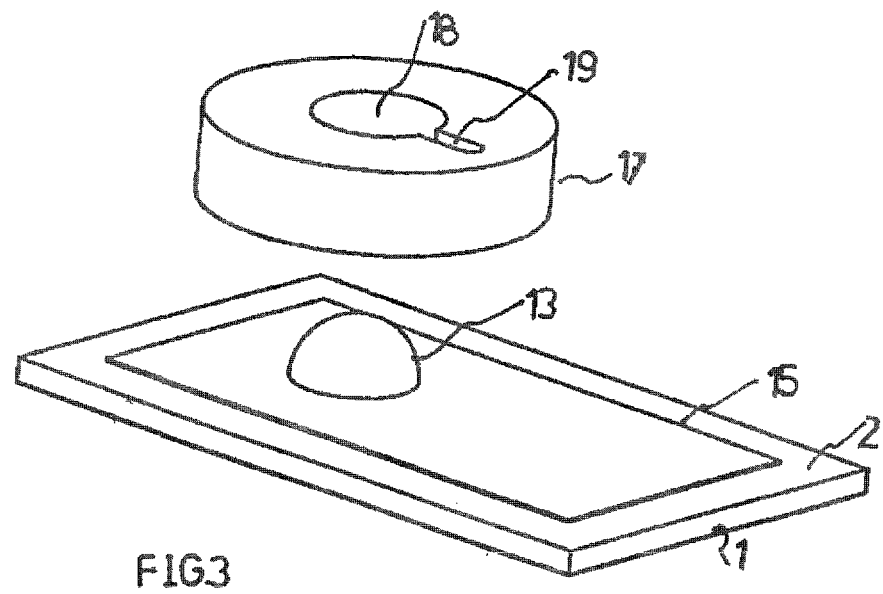
FIGS. 3 and 4 shows the flow cell of FIG. 1 combined with an accessory device.

In the vicinity of the connecting opening 9 formed in the foil layer 5, there is no connection between the fluid reservoir 3 and the support surface 2. A pressing device 17 shown in FIGS. 3 and 4 allows fluid to pass through the connecting opening 9 and enter the passage 10 but prevents fluid flow between the foil layer 5 and the support surface 2.

The pressing element 17 has a passage 18, whose diameter corresponds to the diameter of the storage space 6 or of the projecting spherical cap 13 that forms the storage space 6. A lateral salient projection 19 extends from the passage 18. Its width corresponds to the width of the transport channel 7.

Figure 4:
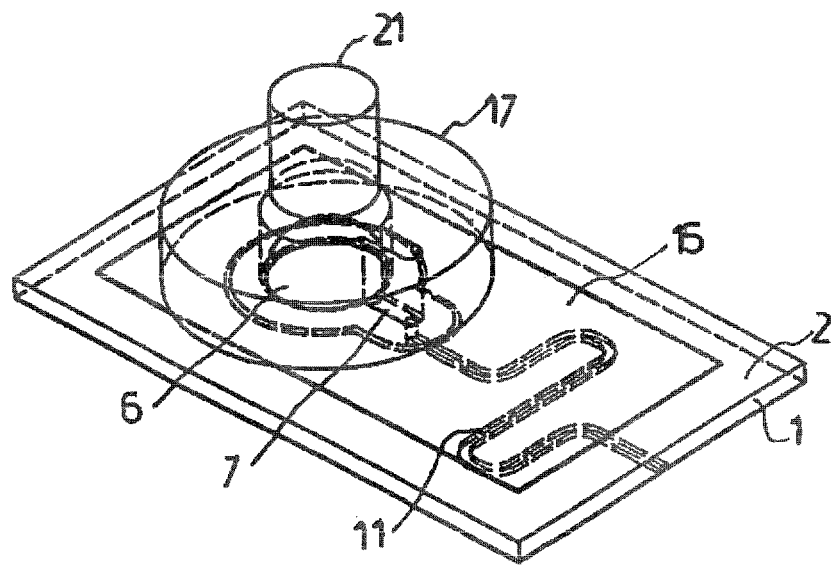

As FIG. 4 shows, the pressing element 17 presses the foil layers 4, 5 together and against the support surface 2. In the area of the storage space 6 and the transport channel 7, in which the foil layer 5 is pressed against the support surface 2 by the fluid pressure, the fluid can pass through the connecting opening 9 only into the passage 10 and not between the foil layer 5 and the support surface 2. A cylindrical pin 21 inserted in the passage 18 allows the storage space 6 to be compressed to eject the fluid.

To even out the pressure, the underside of the pressing element 17 can be provided with an elastic coating.

Figure 5:
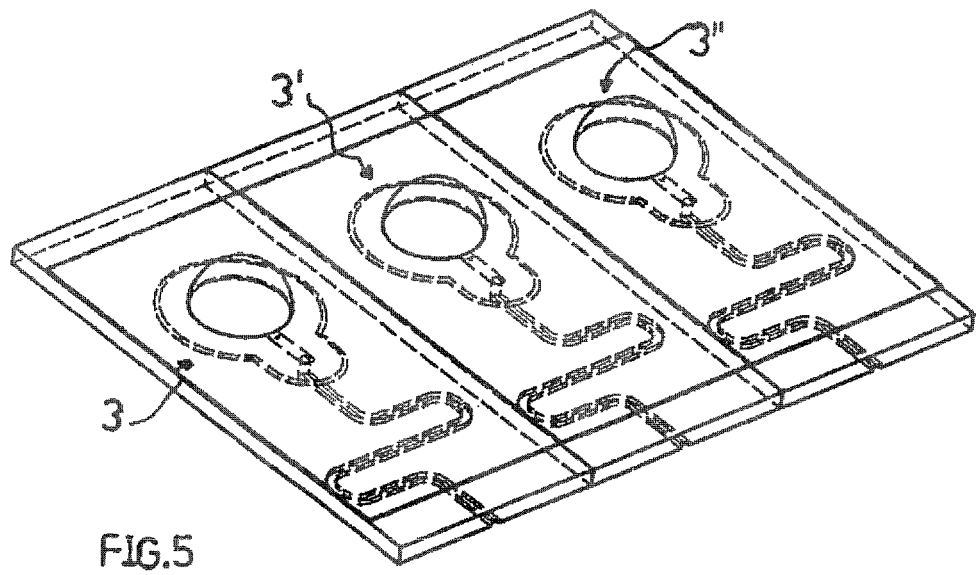
FIG. 5 is an array of flow cells, whose individual sections are flow cells of the type shown in FIG. 1.

FIG. 5 shows a flow cell that combines three cells of the type described above. Accordingly, the flow cell of FIG. 5 has three integrated fluid reservoirs 3, 3′ and 3″.

In the following embodiments, parts that are the same or have the same function are referred to with the same reference numbers as in the preceding embodiments but with the addition of the letter a, b or c to the reference number.

Figure 6:
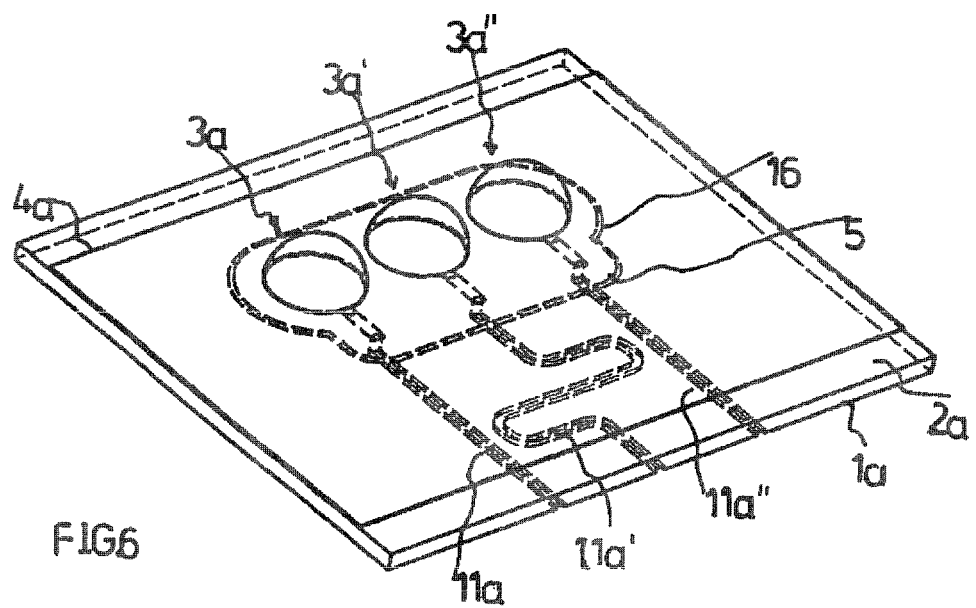
FIG. 6 is another embodiment of a flow cell of the invention.

The flow cell shown in FIG. 6 has a plate-shaped body 1a and three reservoirs 3a, 3a′ and 3a arranged on a support surface 2a. The three reservoirs have a common foil layer 4a and a common foil layer 5a, which is arranged between the foil layer 4a and the support surface 2a.

Figure 7:
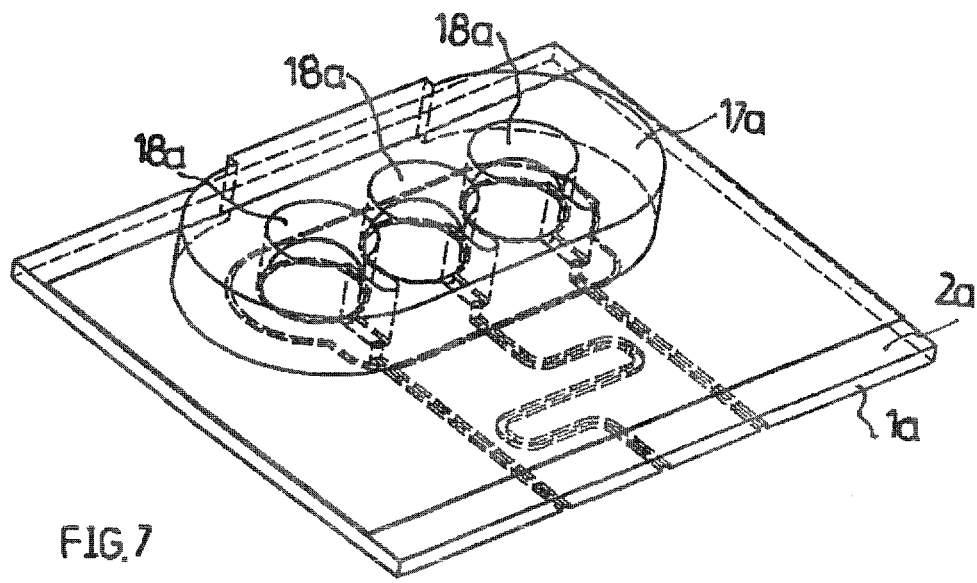
FIG. 7 shows the flow cell of FIG. 6 combined with an accessory device.

As FIG. 7 shows, the flow cell of FIG. 6 can be operated with the use of a pressing element 17a, in which three passages 18a, 18a′ and 18a″ are provided, corresponding to the three fluid reservoirs 3a, 3a′ and 3a″.

Figure 8:
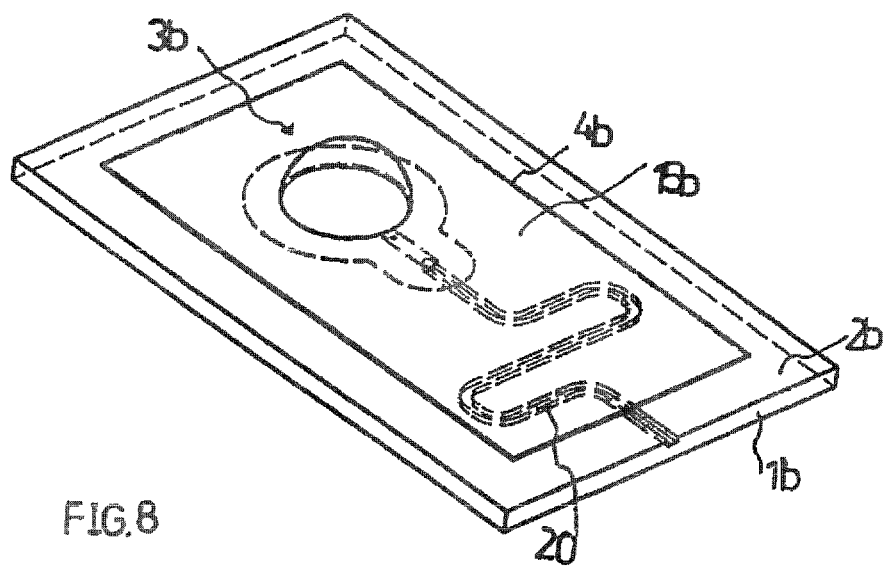
FIG. 8 is a third embodiment of a flow cell of the invention.

FIG. 8 shows an embodiment of a flow cell with a fluid reservoir 3b. It differs from the flow cell of FIG. 1 in that a connecting opening 9b of a transport channel 7b is not connected with a passage perpendicular to the plate but rather is directly connected with a channel 20 that borders on a support surface 2b for the fluid reservoir 3b. The channel, which is formed by a groove, is covered towards the outside by a projecting joining region 15b of a foil layer 4b that faces away from the support surface 2b.

Figure 9:
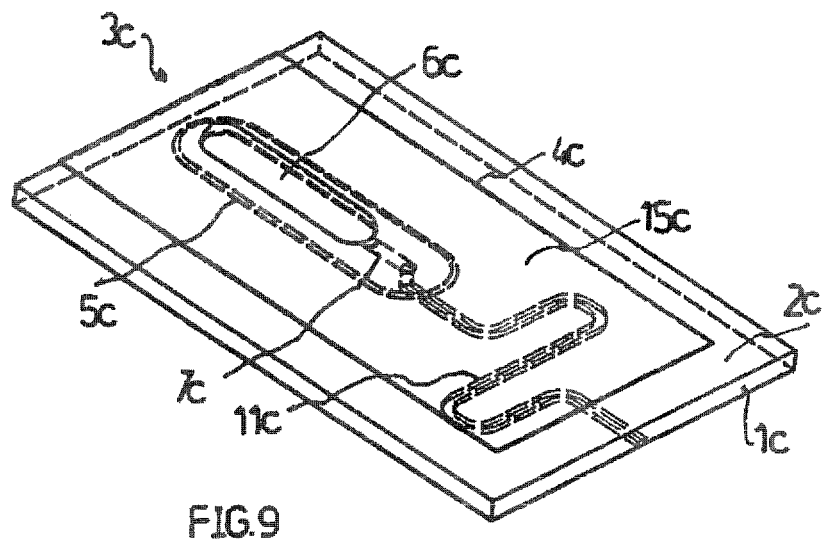
FIG. 9 is a fourth embodiment of a flow cell of the invention.
Figure 10:
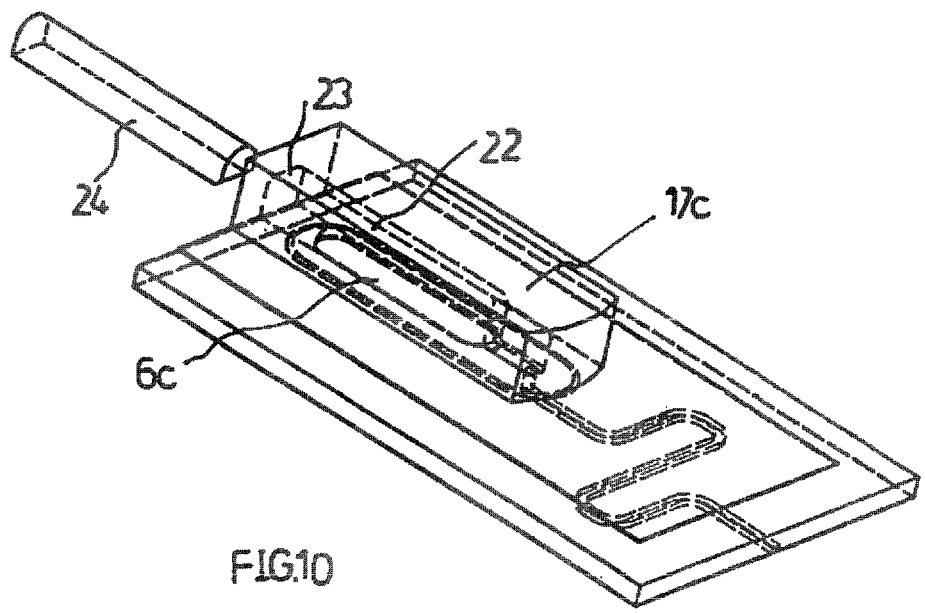
FIG. 10 shows the flow cell of FIG. 9 combined with an accessory device.

FIG. 9 shows an embodiment of a flow cell with an oblong storage space 6c. Accordingly, as FIG. 10 shows, a pressing element 17c is provided with an oblong recess 22 on its side facing the storage space 6c. An oblong slide 24 can be inserted into the open end 23 of the recess 22 to progressively squeeze together the storage space 6c in its longitudinal direction. Therefore, the slide 24 makes it possible to empty the storage space 6c much like a syringe, so that exact metering is made possible by virtue of the fact that a long displacement distance of the slide 24 causes the ejection of only a small volume of fluid per unit distance of the displacement.

It is understood that the reservoir or reservoirs of the flow cells described above can also have the additional functions described in the incorporated application DE 10 2009 005 874.5.

The invention claimed is:

1. A flow cell, comprising: a plate-shaped element that has a flat support surface; and an integrated fluid reservoir made of two foil layers arranged on the support surface of the plate-shaped element and joined with each other to enclose a storage space and a transport channel, wherein the transport channel extends from a burst point that closes the storage space to a connecting opening and can be opened by fluid flowing from the storage space, wherein a first of the foil layers of the fluid reservoir faces away from the support surface and has a region that projects laterally beyond a second of the foil layers of the fluid reservoir that faces the support surface, wherein the first foil layer is bonded with the support surface in the projecting region, wherein the projecting region of the first foil layer surrounds the storage space and the transport channel in spaced relationship to the storage space and the transparent channel.

2. The flow cell in accordance with claim 1, wherein the fluid reservoir is joined with the support surface exclusively by the projecting region.

3. The flow cell in accordance with claim 1, further comprising a welded joint between the fluid reservoir and the support surface.

4. The flow cell in accordance with claim 3, comprising a welded joint between the foil layers.

5. The flow cell in accordance with claim 4, wherein the welded joint is produced by a fusible coating on the foil layer or foil layers.

6. The flow cell in accordance with claim 5, wherein the welding by way of the fusible coating results in formation of a fluidtight joint between the foil layers as well as between the fluid reservoir and the support surface.

7. The flow cell in accordance with claim 1, wherein the foil layer that faces away from the support surface has a shaped section that forms the storage space.

8. The flow cell in accordance with claim 7, wherein the shaped section is a spherical or oblong structure.

9. The flow cell in accordance with claim 1, wherein the foil layer that faces the support surface has a shaped section that forms the storage space, and the plate-shaped element has a depression that takes the shaped section into account.

10. The flow cell in accordance with claim 1, wherein the connecting opening is in direct or indirect fluid connection with a passage perpendicular to the support surface and/or with a channel of the flow cell that is parallel to the support surface.

11. The flow cell in accordance with claim 10, wherein the channel is covered fluidtight by the projecting region of the foil layer that faces away from the support surface.

12. The flow cell in accordance with claim 1, further comprising a pressing element that presses against the support surface, the pressing element including a recess and a sliding element insertable in the recess.

13. The flow cell in accordance with claim 12, wherein the recess has an oblong shape corresponding to the storage space and has an opening at one end for insertion of an oblong sliding element.

14. A fluid reservoir comprising two foils joined with each other to enclose a storage space and a transport channel, wherein one foil projects laterally beyond the other foil, for a flow cell according to claim 1.

15. A method for producing a flow cell with an integrated fluid reservoir that comprises two foil layers arranged on a support surface and joined with each other to enclose a storage space and a transport channel, wherein a first of the foil layers that faces away from the support surface has a region that projects beyond a second of the foil layers of the fluid reservoir that faces the support surface, the method comprising the steps of: prefabricating the fluid reservoir with the foils joined; and joining the prefabricated fluid reservoir with a remainder of the flow cell in the projecting region of the first foil layer with the support surface so that the projecting region of the first foil layer surrounds the storage space and the transport channel in spaced relationship to the storage space and the transparent channel, wherein in the prefabricating step, the first foil layer that faces the support surface is punched out to a final size by limited punch stroke after the first foil layer has been joined with the second foil layer, or the first foil layer is joined in its final dimensions with the second foil layer.

* * * * *